United States Patent
Fridman et al.

(10) Patent No.: US 10,933,405 B2
(45) Date of Patent: Mar. 2, 2021

(54) DEHYDROGENATION CATALYSTS AND METHODS FOR PREPARING AND USING THEM

(71) Applicant: Clariant International Ltd, Muttenz (CH)

(72) Inventors: Vladimir Z. Fridman, Louisville, KY (US); Rong Xing, Louisville, KY (US); Matt Greaney, Hayward, CA (US); David Lowe, Sunnyvale, CA (US); Claus G. Lugmair, Santa Cruz, CA (US)

(73) Assignee: Clariant International Ltd, Muttenz (CH)

(*) Notice: Subject to any disclaimer, the term of this patent is extended or adjusted under 35 U.S.C. 154(b) by 0 days.

(21) Appl. No.: 16/587,173

(22) Filed: Sep. 30, 2019

(65) Prior Publication Data

US 2020/0129961 A1  Apr. 30, 2020

Related U.S. Application Data

(60) Provisional application No. 62/752,380, filed on Oct. 30, 2018.

(51) Int. Cl.

| | | |
|---|---|---|
| *B01J 23/62* | (2006.01) | |
| *B01J 21/12* | (2006.01) | |
| *B01J 37/02* | (2006.01) | |
| *B01J 37/08* | (2006.01) | |
| *C07C 5/333* | (2006.01) | |

(52) U.S. Cl.
CPC ............. *B01J 23/62* (2013.01); *B01J 21/12* (2013.01); *B01J 37/0201* (2013.01); *B01J 37/08* (2013.01); *C07C 5/3337* (2013.01); *C07C 2521/04* (2013.01); *C07C 2521/08* (2013.01); *C07C 2521/12* (2013.01); *C07C 2523/02* (2013.01); *C07C 2523/04* (2013.01); *C07C 2523/08* (2013.01); *C07C 2523/10* (2013.01); *C07C 2523/42* (2013.01); *C07C 2523/58* (2013.01)

(58) Field of Classification Search
CPC ............. B01J 2523/00; B01J 2523/13; B01J 2523/31; B01J 2523/32; B01J 2523/3712; B01J 2523/41; B01J 2523/828; B01J 2523/25; B01J 2523/3706; B01J 21/12; B01J 23/62; B01J 23/63; B01J 23/96; B01J 37/0018; B01J 37/0201; B01J 37/08; B01J 37/088; C07C 5/3337; C07C 11/06; C07C 2521/04; C07C 2521/08; C07C 2521/12; C07C 2523/02; C07C 2523/04; C07C 2523/08; C07C 2523/10; C07C 2523/42; C07C 2523/58; C07C 2523/63

See application file for complete search history.

(56) References Cited

U.S. PATENT DOCUMENTS

| | | |
|---|---|---|
| 3,198,749 A | 8/1965 | Gladrow |
| 4,056,776 A | 11/1977 | Olsson |
| 5,308,822 A | 5/1994 | Iezzi |
| 5,346,871 A | 9/1994 | Robbins |
| 5,414,182 A | 5/1995 | Iezzi |
| 7,235,706 B2 | 6/2007 | Iezzi |
| 7,285,685 B2 | 10/2007 | Walsdorff |
| 8,653,317 B2 | 2/2014 | Howard |
| 9,776,170 B2 | 10/2017 | Kaminsk |
| 9,884,314 B2 | 2/2018 | Luo |
| 2007/0032681 A1* | 2/2007 | Walsdorff ............... B01J 38/14 568/343 |
| 2013/0178682 A1* | 7/2013 | Luo ........................ C07C 5/3335 585/660 |
| 2014/0371501 A1 | 12/2014 | Luo |
| 2019/0089176 A1 | 5/2019 | Xing |
| 2019/0147424 A1 | 5/2019 | Hill et al. |

* cited by examiner

*Primary Examiner* — Sharon Pregler

(57) ABSTRACT

The present disclosure relates to dehydrogenation catalysts based on one or more certain group 13 and group 14 elements that further include additional metal components, to methods for making such catalysts, and to methods for dehydrogenating hydrocarbons using such catalysts. One aspect of the disclosure provides a calcined dehydrogenation catalyst that includes a primary species P1 selected from the group consisting of Ga, In, Tl, Ge, Sn and Pb and combinations thereof; a primary species P2 selected from the lanthanides; a promoter M1 selected from the group consisting of Ni, Pd and Pt; a promoter M2 selected from the group consisting of Li, Na, K, Rb, Cs, Be, Mg, Ca, Sr and Ba, on a silica-alumina support.

20 Claims, No Drawings

DEHYDROGENATION CATALYSTS AND METHODS FOR PREPARING AND USING THEM

BACKGROUND OF THE DISCLOSURE

Field of the Disclosure

This disclosure relates generally to catalyst materials and methods for preparing and using them. More particularly, the present disclosure relates to dehydrogenation catalysts based on one or more certain group 13 and group 14 elements that further include additional metal components, to methods for making such catalysts, and to methods for dehydrogenating hydrocarbons using such catalysts.

Technical Background

Alkane dehydrogenation is a recognized process for production of a variety of useful hydrocarbon products, such as in the dehydrogenation of propane to make propene for use in the polymer industry, dehydrogenation of n-butane to produce n-butene or alkylate and butadiene useful in tire production, and the dehydrogenation of isobutane to make isobutylene suitable for conversion to methyl tert-butyl ether, isooctane, and alkylates to supplement and enrich gasolines. Current commercial catalysts useful for catalytic dehydrogenation of light alkanes include $CrOx/Al_2O_3$ and $Pt$—$Sn/Al_2O_3$ catalysts, which have been in use for decades.

$CrOx/Al_2O_3$ dehydrogenation catalysts typically contain a majority of their chromium in the Cr(III) oxidation state on the alumina surface. However, there typically remains a small amount of Cr(VI), which is carcinogenic and thus presents health risks during catalyst handling and operation. They also can cause significant environmental pollution.

Gallium-based dehydrogenation catalysts have been known for about two decades. They are generally not hazardous, and their application presents no significant environmental issue. However, these catalysts have limitations in activity and stability, especially for the commercially important dehydrogenation of propane.

Accordingly, there remains a need for dehydrogenation catalysts that provide improved activity and stability, especially in the dehydrogenation of propane.

SUMMARY OF THE DISCLOSURE

One aspect of the disclosure is a calcined dehydrogenation catalyst comprising
- a primary species P1 selected from the group consisting of Ga, In, Tl, Ge, Sn, and Pb and combinations thereof, present in the composition in an amount within the range of about 0.05 wt. % to about 20 wt. %, calculated as elemental metal on a calcined basis;
- a primary species P2 selected from the lanthanides, present in the composition in an amount within the range of about 0.05 wt. % to about 10 wt. %, calculated as elemental metal on a calcined basis;
- a promoter M1 selected from the group consisting of Ni, Pd, and Pt, present in the composition in an amount within the range of about 10 ppm to about 500 ppm, calculated as elemental metal on a calcined basis;
- a promoter M2 selected from the group consisting of Li, Na, K, Rb, Cs, Be, Mg, Ca, Sr, and Ba, present in the composition in an amount within the range of about 0.05 wt. % to about 3 wt. %, calculated as elemental metal on a calcined basis; and
- a silica-alumina support S1, present in the composition in an amount within the range of about 60 wt. % to about 99 wt. %, calculated as oxide on a calcined basis.

Another aspect of the disclosure is a method for dehydrogenating hydrocarbons, the method comprising contacting a hydrocarbon feed with a catalyst composition as described herein.

Other aspects of the disclosure will be apparent to the person of ordinary skill in the art in view of the disclosure herein.

DETAILED DESCRIPTION

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. Thus, before the disclosed processes and devices are described, it is to be understood that the aspects described herein are not limited to specific embodiments, apparatuses, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All methods described herein can be performed in any suitable order of steps unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; +19% of the stated value; ±18% of the stated value; +17% of the stated value; +16% of the stated value; ±15% of the stated value; +14% of the stated value; +13% of the stated value; +12% of the stated value; ±11% of the stated value; +10% of the stated value; +9% of the stated value; +8% of the stated value; +7% of the stated value; +6% of the stated value; +5% of the stated value; ±4% of the stated value; +3% of the stated value; +2% of the stated value; or +1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

In various aspects, the disclosure relates to dehydrogenation catalyst compositions that include a primary species selected from certain group 13 and group 14 elements, a primary species selected from the lanthanides, a promoter selected from certain group 10 elements, a promoter selected from certain group 1 and group 2 elements, and a silica-alumina support. The disclosure demonstrates that such catalysts, which may advantageously be free of chromium-containing materials, can exhibit performance comparable to or even better than conventional, commercially available catalysts.

One aspect of the disclosure is a calcined dehydrogenation catalyst composition. The catalyst composition includes a primary species, P1, selected from the group consisting of Ga, In, Tl, Ge, Sn and Pb and combinations thereof, present in the composition in an amount within the range of about 0.05 wt. % to about 20 wt. %, calculated as elemental metal on a calcined basis. The catalyst composition also includes a primary species, P2, selected from the lanthanides (e.g., La, Ce, Nd and combinations thereof), present in the composition in an amount within the range of about 0.05 wt. % to about 10 wt. %, calculated as elemental metal on a calcined basis. The catalyst composition further includes a promoter, M1, selected from the group consisting of Ni, Pd and Pt and combinations thereof, present in the composition in an amount within the range of about 10 ppm to about 500 ppm, calculated as elemental metal on a calcined weight basis. The catalyst composition further includes a promoter, M2, selected from the group consisting of Li, Na, K, Rb, Cs, Be, Mg, Ca, Sr and Ba and combinations thereof, present in the composition in an amount within the range of about 0.05 wt. % to about 3 wt. %, calculated as elemental metal on a calcined basis. And the catalyst composition includes a silica-alumina support, S1, present in the composition in an amount within the range of about 60 wt. % to about 99 wt. %, calculated as oxide on a calcined basis.

As used herein, the terms "alumina" and "silica" include aluminum oxide and silicon oxide, respectively. As used herein, the term "oxide," including, e.g., "mixed oxide," "aluminum oxide," "silicon oxide," etc., includes oxides in all forms and crystalline phases. For example, "aluminum oxide" includes $Al_2O_3$, $Al_2O_x$ wherein x is within the range of 1 to 3, etc. Unless otherwise indicated, regardless of the actual stoichiometry of the oxide, oxides are calculated as the most stable oxide for purposes of weight percent determinations. For example, the person of ordinary skill in the art will appreciate that a non-stoichiometric oxide of aluminum, or even another form of aluminum, may still be calculated as $Al_2O_3$ for purposes of weight percent determinations. Moreover, unless otherwise indicated, the compositions are described on an as-calcined basis.

Without intending to be bound by theory, the present inventors believe that P1 acts as a primary catalytic species in dehydrogenation reactions mediated by the catalyst compositions described herein. As described above, in one aspect of the composition of the disclosure, P1, selected from the group consisting of Ga, In, Tl, Ge, Sn, Pb, and combinations thereof, is present in an amount within the range of about 0.05 wt. % to about 20 wt. %, calculated as elemental metal on a calcined basis. In certain embodiments of the compositions as otherwise described herein, P1 is selected from Ga, Ge, In, Sn, and Tl. For example, in certain embodiments of the compositions as otherwise described herein, P1 is (or includes) Ga. In other embodiments, P1 is (or includes) In, Sn and/or Tl.

In certain embodiments of the compositions as otherwise described herein, P1 is present in the composition in an amount within the range of about 0.05 wt. % to about 17.5 wt. %, or about 0.05 wt. % to about 15 wt. %, or about 0.05 wt. % to about 12.5 wt. %, or about 0.05 wt. % to about 10 wt. %, or about 0.05 wt. % to about 7.5 wt. %, or about 0.05 wt. % to about 5 wt. %, or about 0.1 wt. % to about 20 wt. %, or about 0.25 wt. % to about 20 wt. %, or about 0.5 wt. % to about 20 wt. %, or about 0.75 wt. % to about 20 wt. %, or about 1 wt. % to about 20 wt. %, or about 1.5 wt. % to about 20 wt. %, or about 2 wt. % to about 20 wt. %, or about 2.5 wt. % to about 20 wt. %, or about 5 wt. % to about 20 wt. %, or about 7.5 wt. % to about 20 wt. %, or about 10 wt. % to about 20 wt. %, or about 12.5 wt. % to about 20 wt. %, or about 15 wt. % to about 20 wt. %, or about 0.1 wt. % to about 17.5 wt. %, or about 0.1 wt. % to about 15 wt. %, or about 0.1 wt. % to about 12.5 wt. %, or about 0.1 wt. % to about 10 wt. %, or about 0.5 wt. % to about 7.5 wt. %, calculated as elemental metal on a calcined basis.

Without intending to be bound by theory, the present inventors believe that P2 acts as a primary catalytic species in dehydrogenation reactions mediated by the catalyst compositions described herein. As described above, in one aspect of the compositions of the disclosure, P2, selected from the lanthanides, is present in an amount within the range of about 0.05 wt. % to about 10 wt. %, calculated as elemental metal on a calcined basis. In certain embodiments of the compositions as otherwise described herein, P2 is selected from La, Ce, and Nd. For example, in certain embodiments of the compositions as otherwise described herein, P2 is (or includes) Ce. In other embodiments of the compositions as otherwise described herein, P2 is (or includes) La. For example, in certain embodiments of the compositions as otherwise described herein, P2 is (or includes) Ce and La. In other embodiments of the compositions as otherwise described herein, P2 is (or includes) Nd.

In certain embodiments of the compositions as otherwise described herein, P2 is present in the composition in an amount within the range of about 0.05 wt. % to about 9 wt. %, or about 0.05 wt. % to about 8 wt. %, or about 0.05 wt. % to about 7 wt. %, or about 0.05 wt. % to about 6 wt. %, or about 0.05 wt. % to about 5 wt. %, or about 0.05 wt. % to about 4 wt. %, or about 0.05 wt. % to about 3 wt. %, or about 0.05 wt. % to about 2 wt. %, or about 0.05 wt. % to about 1 wt. %, or about 0.1 wt. % to about 10 wt. %, or about 0.25 wt. % to about 10 wt. %, or about 0.5 wt. % to about 10 wt. %, or about 0.75 wt. % to about 10 wt. %, or about 1 wt. % to about 10 wt. %, or about 1.5 wt. % to about 10 wt. %, or about 2 wt. % to about 10 wt. %, or about 3 wt. % to about 10 wt. %, or about 4 wt. % to about 10 wt. %, or about 5 wt. % to about 10 wt. %, or about 0.1 wt. % to about 9 wt. %, or about 0.1 wt. % to about 8 wt. %, or about 0.1 wt. % to about 7 wt. %, or about 0.1 wt. % to about 6 wt. %, or about 0.25 wt. % to about 5 wt. %, calculated as elemental metal on a calcined basis.

As described above, in one aspect of the compositions of the disclosure, M1, selected from the group consisting of Ni, Pd, and Pt, is present in an amount within the range of about 10 ppm to about 500 ppm, calculated as elemental metal on a calcined weight basis. In certain embodiments of the compositions as otherwise described herein, M1 is selected from Pd and Pt. For example, in certain embodiments of the compositions as otherwise described herein, M1 is (or includes) Pt. In other embodiments of the compositions as otherwise described herein, M1 is (or includes) Pd.

In certain embodiments of the compositions as otherwise described herein, M1 is present in the composition in an amount within the range of about 10 ppm to about 450 ppm, or about 10 ppm to about 400 ppm, or about 10 ppm to about 350 ppm, or about 10 ppm to about 300 ppm, or about 10 ppm to about 250 ppm, or about 10 ppm to about 200 ppm, or about 10 ppm to about 150 ppm, or about 10 ppm to about 100 ppm, or about 25 ppm to about 500 ppm, or about 50 ppm to about 500 ppm, or about 75 ppm to about 500 ppm, or about 100 ppm to about 500 ppm, or about 150 ppm to about 500 ppm, or about 200 ppm to about 500 ppm, or about 250 ppm to about 500 ppm, or about 300 ppm to about 500 ppm, or about 250 ppm to about 500 ppm, or about 25 ppm to about 450 ppm, or about 50 ppm to about 400 ppm, or about 75 ppm to about 350 ppm, or about 100 ppm to about 300 ppm, calculated as elemental metal on a calcined weight basis.

As described above, in one aspect of the compositions of the disclosure, M2, selected from the group the group consisting of Li, Na, K, Rb, Cs, Be, Mg, Ca, Sr and Ba, is present in an amount within the range of about 0.05 wt. % to about 3 wt. %, calculated as elemental metal on a calcined basis. In certain embodiments of the compositions as otherwise described herein, M2 is selected from Li, Na, K, Cs, and Ba. For example, in certain embodiments of the compositions as otherwise described herein, M2 is (or includes) K. In one example, in certain embodiments of the compositions as otherwise described herein, M2 is (or includes) Ba and K (e.g., where P2 is, or includes, Ce).

In certain embodiments of the compositions as otherwise described herein, M2 is present in the composition in an amount within the range of about 0.05 wt. % to about 2.75 wt. %, or about 0.05 wt. % to about 2.5 wt. %, or about 0.05 wt. % to about 2.25 wt. %, or about 0.05 wt. % to about 2 wt. %, or about 0.05 wt. % to about 1.75 wt. %, or about 0.05 wt. % to about 1.5 wt. %, or about 0.05 wt. % to about 1.25 wt. %, or about 0.05 wt. % to about 1 wt. %, or about 0.1 wt. % to about 3 wt. %, or about 0.25 wt. % to about 3 wt. %, or about 0.5 wt. % to about 3 wt. %, or about 0.75 wt. % to about 3 wt. %, or about 1 wt. % to about 3 wt. %, or about 1.25 wt. % to about 3 wt. %, or about 1.5 wt. % to about 3 wt. %, or about 1.75 wt. % to about 3 wt. %, or about 2 wt. % to about 3 wt. %, or about 0.1 wt. % to about 2.5 wt. %, or about 0.1 wt. % to about 2 wt. %, or about 0.1 wt. % to about 1.75 wt. %, or about 0.1 wt. % to about 1.5 wt.

%, or about 0.1 wt. % to about 1.25 wt. %, or about 0.1 wt. % to about 1 wt. %, calculated as elemental metal on a calcined basis.

For example, in certain embodiments of the compositions as otherwise described herein, P1 (e.g., Ga) is present in the composition in an amount within the range of about 0.1 wt. % to about 10 wt. %, about 0.5 wt. % to about 9 wt. %, about 0.75 wt. % to about 8 wt. %, or about 1 wt. % to about 7 wt. %, calculated as elemental metal on a calcined basis. In certain such embodiments, P2 (e.g., Ce, or La and Ce) is present in the composition in an amount within the range of about 0.1 wt. % to about 6 wt. %, about 0.25 wt. % to about 5 wt. %, about 0.5 wt. % to about 4 wt. %, or about 0.75 wt. % to about 3 wt. %, calculated as elemental metal on a calcined basis. In certain such embodiments, M1 (e.g., Pt) is present in the composition in an amount within the range of about 50 ppm to about 400 ppm, about 75 ppm to about 350 ppm, or about 100 ppm to about 300 ppm, calculated as elemental metal on a calcined weight basis. In certain such embodiments, M2 (e.g., K, or K and Ba) is present in the composition in an amount within the range of about 0.05 wt. % to about 2 wt. %, or about 0.05 wt. % to about 1.5 wt. %, or about 0.1 wt. % to about 1 wt. %, calculated as elemental metal on a calcined basis.

As described above, in certain aspects of the compositions of the disclosure, a silica-alumina support S1 is present in the composition. The person of ordinary skill in the art will appreciate that, as used herein, a "silica-alumina" support (e.g., S1) comprises a mixture of silica and alumina. The person of ordinary skill in the art will further appreciate that a "mixture" of silica and alumina includes homogeneous and heterogeneous mixtures. For example, the silica-alumina support S1 may comprise a covalently bound network including both silicon and aluminum atoms (e.g., —Si—O—Al—), or discrete domains of both silica and alumina.

In certain embodiments of the compositions as otherwise described herein, the amount of silica present in S1 is within the range of about 1 wt. % to about 70 wt. % of S1. For example, in certain embodiments of the compositions as otherwise described herein, the amount of silica present in S1 is within the range of about 1 wt. % to about 65 wt. %, or about 1 wt. % to about 60 wt. %, or about 1 wt. % to about 55 wt. %, or about 1 wt. % to about 50 wt. %, or about 1 wt. % to about 40 wt. %, or about 1 wt. % to about 30 wt. %, or about 1 wt. % to about 20 wt. %, or about 1 wt. % to about 10 wt. %, or about 2.5 wt. % to about 70 wt. %, or about 5 wt. % to about 70 wt. %, or about 7.5 wt. % to about 70 wt. %, or about 10 wt. % to about 70 wt. %, or about 15 wt. % to about 70 wt. %, or about 20 wt. % to about 70 wt. %, or about 30 wt. % to about 70 wt. %, or about 40 wt. % to about 70 wt. % of S1, or about 50 wt. % to about 70 wt. %. In certain embodiments of the compositions as otherwise described herein, the amount of alumina present in S1 is within the range of about 30 wt. % to about 99 wt. % of S1. For example, in certain embodiments of the compositions as otherwise described herein, the amount of alumina present in S1 is within the range of about 30 wt. % to about 97.5 wt. %, or about 30 wt. % to about 95 wt. %, or about 30 wt. % to about 90 wt. %, or about 30 wt. % to about 85 wt. %, or about 30 wt. % to about 80 wt. %, or about 30 wt. % to about 70 wt. %, or about 30 wt. % to about 60 wt. %, or about 40 wt. % to about 99 wt. %, or about 50 wt. % to about 99 wt. %, or about 60 wt. % to about 99 wt. %, or about 70 wt. % to about 99 wt. %, or about 80 wt. % to about 99 wt. %, or about 85 wt. % to about 99 wt. %, or about 90 wt. % to about 99 wt. %, or about 50 wt. % to about 97.5 wt. %, or about 60 wt. % to about 95 wt. %, or about 70 wt. % to about 90 wt. %.

In certain embodiments of the compositions as otherwise described herein, the total amount of alumina and silica in S1 is at least about 80 wt. % of S1. For example, in certain embodiments of the compositions as otherwise described herein, the total amount of alumina and silica in S1 is at least about 85 wt. %, at least about 90 wt. %, at least about 92.5 wt. %, at least about 95 wt. %, at least about 97.5 wt. %, at least about 98 wt. %, or at least about 99 wt. % of S1.

As described above, in one aspect of the compositions of the disclosure, silica-alumina support S1 is present in an amount within the range of about 60 wt. % to about 99 wt. %, calculated as oxide on a calcined basis. In certain embodiments of the compositions as otherwise described herein, S1 is present in an amount within the range of about 60 wt. % to about 97.5 wt. %, or about 60 wt. % to about 95 wt. %, or about 60 wt. % to about 90 wt. %, or about 60 wt. % to about 85 wt. %, or about 60 wt. % to about 80 wt. %, or about 60 wt. % to about 75 wt. %, or about 65 wt. % to about 99 wt. %, or about 70 wt. % to about 99 wt. %, or about 75 wt. % to about 99 wt. %, or about 80 wt. % to about 99 wt. %, or about 85 wt. % to about 99 wt. %, or about 90 wt. % to about 99 wt. %.

In certain embodiments as otherwise described herein, P1 includes Ga, and if P2 includes Ce, the dehydrogenation catalyst includes one or more of La and Ba.

In certain embodiments as otherwise described herein, P1 includes Ga, P2 includes Ce, and the dehydrogenation catalyst includes one or more of La and Ba.

The person of ordinary skill in the art will appreciate that the catalyst composition may, in some embodiments as otherwise described herein, be substantially free of Cr. Chromium-free compositions are especially desirable from an environmental perspective. For example, in certain embodiments of the compositions as otherwise described herein, the catalyst composition includes less than about 1 wt. %, or less than about 0.9 wt. %, or less than about 0.8 wt. %, or less than about 0.7 wt. %, or less than about 0.6 wt. %, or less than about 0.5 wt. %, or less than about 0.4 wt. %, or less than about 0.3 wt. %, or less than about 0.2 wt. %, or less than about 0.1 wt. %, or less than about 0.05 wt. %, or less than about 0.01 wt. % of Cr, calculated as $Cr_2O_3$ on a calcined basis.

The present inventors have determined that suitable dehydrogenation catalysts can be made using the P1, P2, M1, M2 and S1 components described herein, e.g., in some embodiments without the use of other promotor or catalytic species. In certain desirable embodiments of the compositions as otherwise described herein, the total amount of the primary species (e.g., P1 and P2), promoters (e.g., M1 and M2), and support (e.g., S1) is at least about 80 wt. %, or at least about 85 wt. %, or at least about 90 wt. %, or at least about 95 wt. %, or at least about 97 wt. %, or at least about 98 wt. %, or at least about 99 wt. %, or at least about 99.5 wt. % of the composition (i.e., P1, P2, M1, and M2 calculated as elemental metal and S1 calculated as oxide on a calcined basis).

In certain desirable embodiments of the compositions as otherwise described herein, S1 comprises a covalent network structure, throughout which structure one or more of the primary species (e.g., P1 and P2) and promoters (e.g., M1 and M2) are dispersed.

Another aspect of the disclosure is a method for preparing a dehydrogenation catalyst composition as described herein. Conventional methods can be adapted for use in preparing the dehydrogenation catalysts of the disclosure. For example, various hydrolysis-polycondensation, precipitation and impregnation processes can be used, singly or in combination, to provide the compositions. Silica-alumina support materials can suitably be made, for example, by a hydrolysis-polycondensation process (e.g., from one or more hydroxide or oxy compounds). Certain of the P1, P2, M1 and M2 species can be formulated together with the silica-alumina support through hydrolysis-polycondensation. P1, P2, M1 and M2 species can alternatively or additionally be provided to the support through impregnation.

For example, in certain embodiments, a method for making a dehydrogenation catalyst as described herein includes providing a silica-alumina support S1 (e.g., the product of a hydrolysis-polycondensation reaction of one or more silicon and aluminum oxy compounds), impregnating the silica-alumina support S1 with P1, P2, M1 and M2 via one or more impregnation steps to provide the desired amounts of P1, P2, M1 and M2 in the final catalyst. In each such impregnation step, a impregnation solution (e.g., an aqueous impregnation solution) containing one or more of a P1 source, a P2 source, an M1 source, and an M2 source, is contacted with the support. After removal of the solution from the impregnated support, it can be dried and/or calcined. In certain such embodiments, providing the silica-alumina support S1 comprises reacting one or more S1 sources, e.g., in a hydrolysis-polycondensation reaction, with the S1 sources being one or more oxy compounds, e.g., oxides (e.g., alumina, silica), alkoxides (e.g., tetraethyl orthosilicate, aluminum isopropoxide), oxynitrates, nitrates, acetylacetonates, or hydroxides (e.g., aluminum hydroxide). The amounts and identities of the various components (e.g., P1, P2, M1, M2, and S1) can be as otherwise described above with respect to the catalyst composition of the disclosure (i.e., measured with respect to final catalyst composition).

In another example, in various aspects and embodiments, the method includes reacting an S1 source (e.g., as otherwise described herein) in the presence of one or more of a P1 source, a P2 source, an M1 source, and an M2 source, and calcining the reaction product to provide an silica-alumina support S1 formulated with one or more of P1, P2, M1 and M2. One or more of a P1 source, a P2 source, an M1 source, and an M2 source can then be provided to the calcined reaction product via one or more impregnation steps to provide the desired amounts of P1, P2, M1 and M2 in the final catalyst (i.e., each coming from being formulated together with the support, added via impregnation, or a combination thereof). The amounts and identities of the various components (e.g., P1, P2, M1, M2, S1) can be as otherwise described above with respect to the catalyst composition of the disclosure.

In certain embodiments of the methods as otherwise described herein, the method comprises impregnating a silica-alumina support S1 with an impregnation solution comprising a P1 salt (e.g., a gallium salt) to form a P1-formulated (e.g., Ga-formulated) support S1. In other embodiments of the methods as otherwise described herein, the method comprises reacting an S1 source in the presence of a P1 source, for example, by acidifying an aqueous mixture of aluminum hydroxide, silica, and gallium (e.g., in the form of a nitrate, isopropoxide or acetylacetonate) and calcining the reaction product to provide a silica-alumina support S1 formulated with P1 (e.g., Ga).

In certain embodiments of the methods as otherwise described herein, the method comprises impregnating a silica-alumina support S1 with an impregnation solution comprising a P2 salt (e.g., a cerium salt and/or a lanthanum salt) to provide a P2-formulated support S1. In other embodiments of the methods as otherwise described herein, the method comprises reacting an S1 source in the presence of a P2 source, for example, by acidifying an aqueous mixture of aluminum hydroxide, silica, *allium* (e.g., in the form of a nitrate, isopropoxide or acetylacetonate) and cerium and/or lanthanum (e.g., in the form of isopropoxide, acetylacetonate or nitrate), and calcining the reaction product to provide a silica-alumina support S1 formulated with P2 (e.g., Ce or La).

In certain embodiments of the methods as otherwise described herein, the method comprises reacting an S1 source in the presence of a P1 source and a P2 source, for example, by acidifying an aqueous mixture of aluminum hydroxide, silica, cerium and/or lanthanum (e.g., in the form of isopropoxide, acetylacetonate or nitrate), and calcining the reaction product to provide a silica-alumina support S1 formulated with P1 and P2 (e.g., gallium and cerium and/or lanthanum).

In certain embodiments, a method for preparing a dehydrogenation catalyst as described herein includes providing a silica-alumina support S1 formulated with P1 (e.g., Ga). The formulation with P1 can be through an initial impregnation step, or through reaction of a P1 source together with the S1 source(s). The P1-formulated silica-alumina support S1 can be impregnated with P2, M1 and M2 (e.g., using an impregnation solution comprising a P2 source, an M1 source and an M2 source). In certain such embodiments, when Ce is present in the dehydrogenation catalyst, support is impregnated with one or more of Ba and La. The impregnated material can then be calcined.

In certain embodiments, a method for preparing a dehydrogenation catalyst as described herein includes providing a silica-alumina support S1 formulated with P1 (e.g., Ga) and P2 (e.g., Ce). The formulation with P1 and P2 can be through an initial impregnation step, or through reaction of P1 source and P2 sources together with the S1 source(s). The P1/P2-formulated silica-alumina support S1 can be impregnated with M1 and M2 (e.g., using an impregnation solution comprising an M1 source and an M2 source). In certain such embodiments, the support is impregnated with one or more of Ba and La. The impregnated material can then be calcined.

In certain embodiments of the methods as otherwise described herein, the P1 source is a gallium salt, e.g., gallium nitrate, gallium isopropoxide, or gallium acetylacetonate.

In certain embodiments of the methods as otherwise described herein, the P2 source is a salt. For example, in certain embodiments of the methods as otherwise described herein, the P2 source is a cerium salt, e.g., cerium nitrate, cerium isopropoxide or cerium acetylacetonate. In another example, in certain embodiments of the methods as otherwise described herein, the P2 source is a lanthanum salt, e.g., cerium nitrate, cerium isopropoxide or cerium acetylacetonate.

In certain embodiments of the methods as otherwise described herein, the M1 source is a salt. For example, in certain embodiments of the methods as otherwise described herein, the M1 source is a platinum salt, e.g., $Pt(NH_3)_4(NO_3)_2$ or $H_2PtCl_4$. In another example, in certain embodiments of the methods as otherwise described herein, the M1 source is a palladium salt, e.g., $Pd(NO_3)_2$.

In certain embodiments of the methods as otherwise described herein, the M2 source is a salt. For example, in certain embodiments of the methods as otherwise described herein, the M1 source is a salt of a group 1 element, e.g., KNO$_3$. In another example, in certain embodiments of the methods as otherwise described herein, the M2 source is a salt of a group 2 element, e.g., Mg(NO$_3$)$_2$, Ca(NO$_3$)$_2$, Sr(NO$_3$)$_2$, or Ba(NO$_3$)$_2$.

While particular salt species have been described above, the person of ordinary skill in the art will appreciate that other salts and other metallic can be used in the methods described herein.

As described above, the method includes calcining the impregnated silica-alumina support S1. In certain embodiments of the methods as otherwise described herein, the impregnated silica-alumina support S1 is calcined at a temperature within the range of about 300° C. to about 900° C. For example, in certain embodiments, the impregnated support S1 is calcined at a temperature within the range of about 350° C. to about 900° C., or about 400° C. to about 900° C., or about 450° C. to about 900° C., or about 500° C. to about 900° C., or about 550° C. to about 900° C., or about 300° C. to about 850° C., or about 300° C. to about 800° C., or about 300° C. to about 750° C., or about 300° C. to about 700° C., or about 300° C. to about 650° C., or about 350° C. to about 850° C., or about 400° C. to about 800° C., or about 450° C. to about 750° C.

In certain embodiments of the methods as otherwise described herein, the impregnated silica-alumina support S1 is calcined for a period of time within the range of about 5 min. to about 12 hr. For example, in certain embodiments of the methods as otherwise described herein, the impregnated support S1 is calcined for a period of time within the range of about 10 min. to about 12 hr., or about 15 min. to about 12 hr., or about 20 min. to about 12 hr., or about 30 min. to about 12 hr., or about 45 min. to about 12 hr., or about 1 hr. to about 12 hr., or about 1.5 hr. to about 12 hr., or about 2 hr. to about 12 hr., or about 5 min. to about 11 hr., or about 5 min. to about 10 hr., or about 5 min. to about 9 hr., or about 5 min. to about 8 hr., or about 5 min. to about 7.5 hr., or about 5 min. to about 7 hr., or about 5 min. to about 6.5 hr., or about 5 min. to about 6 hr., or about 5 min. to about 5.5 hr., or about 5 min. to about 5 hr., or about 30 min. to about 11 hr., or about 1 hr. to about 10 hr., or about 1.5 hr. to about 9 hr., or about 2 hr. to about 8 hr.

In certain embodiments of the methods as otherwise described herein, the impregnated silica-alumina support S1 is dried before calcination. In certain embodiments of the methods as otherwise described herein, the impregnated support S1 is dried at a temperature within the range of about 80° C. to about 240° C. For example, in certain embodiments of the methods as otherwise described herein, the impregnated support S1 is dried at a temperature within the range of about 80° C. to about 220° C., or about 80° C. to about 200° C., or about 80° C. to about 180° C., or about 100° C. to about 240° C., or about 120° C. to about 240° C., or about 140° C. to about 240° C., or about 100° C. to about 220° C., or about 120° C. to about 200° C., or about 140° C. to about 180° C.

In certain embodiments of the methods as otherwise described herein, the impregnated silica-alumina support S1 is dried for a period of time within the range of about 4 hr. to about 36 hr. For example, in certain embodiments of the methods as otherwise described herein, the impregnated support S1 is dried for a period of time within the range of about 4 hr. to about 30 hr., or about 4 hr. to about 24 hr., or about 4 hr. to about 22 hr., or about 4 hr. to about 20 hr., or about 6 hr. to about 36 hr., or about 8 hr. to about 36 hr., or about 10 hr. to about 36 hr., or about 12 hr. to about 36 hr., or about 6 hr. to about 30 hr., or about 8 hr. to about 24 hr., or about 10 hr. to about 22 hr., or about 12 hr. to about 20 hr.

Another aspect of the disclosure is a catalyst composition prepared by a method as described herein.

Advantageously, the present inventors have determined that the use of catalyst compositions described herein can catalyze a hydrocarbon dehydrogenation reaction at an efficiency comparable to or better than conventional, commercially available catalyst materials.

The compositions described herein are especially useful in hydrocarbon dehydrogenation reactions. Accordingly, another aspect of the disclosure is a method for dehydrogenating alkanes that includes contacting a hydrocarbon feed with a catalyst composition as described herein under conditions sufficient to cause hydrocarbon dehydrogenation.

In some embodiments of the dehydrogenation methods as otherwise described herein, the hydrocarbon feed comprises one or more $C_3$-$C_5$ alkanes. For example, in certain embodiments of the dehydrogenation methods as otherwise described herein, the hydrocarbon feed comprises propane.

The contacting of the feed with the catalyst compositions described herein can be conducted in a variety of ways familiar to the person of ordinary skill in the art. Conventional equipment and processes can be used in conjunction with the catalyst compositions of the disclosure to provide beneficial performance. Thus, the catalyst may be contained in one bed within a reactor vessel or divided up among a plurality of beds within a reactor. The reaction system may contain one or more reaction vessels in series. The feed to the reaction zone can flow vertically upwards, or downwards through the catalyst bed in a typical plug flow reactor, or horizontally across the catalyst bed in a radial flow type reactor.

The contacting of the feed with the catalyst composition can be performed using conventional methods. For example, the feed may be introduced into the reaction zone containing the catalyst composition at a constant rate, or alternatively, at a variable rate.

In certain embodiments of the dehydrogenation methods as otherwise described herein, the feed is contacted with the provided catalyst composition at a liquid hourly space velocity (LHSV) within the range of about 0.5 h$^{-1}$ to about 4 h$^{-1}$. For example, in certain embodiments of the dehydrogenation methods as otherwise described herein, the feed is contacted with the provided catalyst composition at a liquid hourly space velocity of about 0.75 h$^{-1}$ to about 4 h$^{-1}$, or about 1 h$^{-1}$ to about 4 h$^{-1}$, or about 1.25 h$^{-1}$ to about 4 h$^{-1}$, or about 1.5 h$^{-1}$ to about 4 h$^{-1}$, or about 0.5 h$^{-1}$ to about 3.75 h$^{-1}$, or about 0.5 h$^{-1}$ to about 3.5 h$^{-1}$, or about 0.5 h$^{-1}$ to about 3.25 h$^{-1}$, or about 0.5 h$^{-1}$ to about 3 h$^{-1}$, or about 0.5 h$^{-1}$ to about 2.75 h$^{-1}$, or about 0.5 h$^{-1}$ to about 2.5 h$^{-1}$, or about 0.75 h$^{-1}$ to about 3.5 h$^{-1}$, or about 1 h$^{-1}$ to about 3 h$^{-1}$, or about 1.25 h$^{-1}$ to about 2.75 h$^{-1}$, or about 1.5 h$^{-1}$ to about 2.5 h$^{-1}$.

In certain embodiments of the dehydrogenation methods as otherwise described herein, the method is carried out at a temperature within the range of about 400° C. to about 750° C. For example, in certain embodiments of the dehydrogenation methods as otherwise described herein, the method is carried out at a temperature within the range of about 400° C. to about 700° C., or about 400° C. to about 650° C., or about 400° C. to about 600° C., or about 400° C. to about 550° C., or about 450° C. to about 750° C., or about 500° C. to about 750° C., or about 550° C. to about 750° C., or about 600° C. to about 750° C., or about 450° C. to about 700° C., or about 500° C. to about 650° C.

In certain embodiments of the dehydrogenation methods as otherwise described herein, the method is carried out at a pressure within the range of about 0.1 bar to about 1 bar. For example, in certain embodiments of the dehydrogenation methods as otherwise described herein, the methods is carried out at a pressure within the range of about 0.1 bar to about 0.9 bar, or about 0.1 bar to about 0.8 bar, or about 0.1 bar to about 0.7 bar, or about 0.1 bar to about 0.6 bar, or about 0.1 bar to about 0.5 bar, or about 0.2 bar to about 1 bar, or about 0.3 bar to about 1 bar, or about 0.4 bar to about 1 bar, or about 0.5 bar to about 1 bar, or about 0.2 bar to about 0.9 bar, or about 0.3 bar to about 0.8 bar, or about 0.4 bar to about 0.7 bar.

EXAMPLES

The Examples that follow are illustrative of specific embodiments of the invention, and various uses thereof. They are set forth for explanatory purposes, only, and are not to be taken as limiting the invention.

Example 1. Catalyst Preparation

A silica-alumina support was prepared via sol-gel synthesis: 89.4 g aluminum isopropoxide was added to 848 g DI water heated to 90° C. 9.8 g tetraethyl orthosilicate was added to the mixture, which was then stirred at 90° C. for 30 minutes. An aqueous solution of 18.0 g $HNO_3$ and 5.5 g DI water was added to the mixture, which was then stirred vigorously for 75 min. at 86-90° C. to provide a concentrated slurry/gel. The composition was dried in air at 120° C. for 16 hours and calcined at 600° C. in air for 4 hours, to provide a silica-alumina support containing 10 wt. % silica. Catalyst A1 was made by impregnation of the silica-alumina support with an aqueous solution containing $Ga(NO_3)_3$, $KNO_3$, $Ce(NO_3)_3.6H_2O$, and $Pt(NH_3)_4(NO_3)_2$ by incipient wetness. The catalyst was dried in air at room temperature for at least 1 hour and calcined in air at 750° C. for 1 hour.

A silica-alumina support was prepared via sol-gel synthesis: 72.3 g aluminum isopropoxide was added to 848 g DI water heated to 90° C. 28 g tetraethyl orthosilicate was added to the mixture, which was then stirred at 90° C. for 30 minutes. An aqueous solution of 18.0 g $HNO_3$ and 5.5 g DI water was added to the mixture, which was then stirred vigorously for 3 hours at 86-90° C. to provide a concentrated slurry/gel. The composition was dried in air at 120° C. for 16 hours and calcined at 600° C. in air for 4 hours, to provide a silica-alumina support containing 25 wt. % silica. Catalyst A2 was made by impregnation of the silica-alumina support with an aqueous solution containing $Ga(NO_3)_3$, $KNO_3$, $Ce(NO_3)_3.6H_2O$, and $Pt(NH_3)_4(NO_3)_2$ by incipient wetness. The catalyst was dried in air at room temperature for at least 1 hour and calcined in air at 750° C. for 1 hour.

Catalyst A3 was made by impregnation of a silica-alumina support containing 5 wt. % silica (Sasol Siralox 5) with an aqueous solution containing $Ga(NO_3)_3$, $KNO_3$, $Ce(NO_3)_3.6H_2O$, and $Pt(NH_3)_4(NO_3)_2$ by incipient wetness. The catalyst was dried in air at room temperature for at least 1 hour and calcined in air at 750° C. for 1 hour.

Catalyst A4 was made by impregnation of a silica-alumina support containing 5 wt. % silica (Sasol Siralox 5) with an aqueous solution containing $Ga(NO_3)_3$, $KNO_3$, $Ce(NO_3)_3.6H_2O$, and $Pt(NH_3)_4(NO_3)_2$ by incipient wetness. The catalyst was dried in air at room temperature for at least 1 hour and calcined in air at 750° C. for 1 hour.

Catalyst A5 was made by impregnation of a silica-alumina support containing 10 wt. % silica (Sasol Siralox 10) with an aqueous solution containing $Ga(NO_3)_3$, $KNO_3$, $Ce(NO_3)_3.6H_2O$, and $Pt(NH_3)_4(NO_3)_2$ by incipient wetness. The catalyst was dried in air at room temperature for 1 hour and calcined in air at 750° C. for 1 hour.

Catalyst A6 was made by impregnation of a silica-alumina support containing 10 wt. % silica (Sasol Siralox 10) with an aqueous solution containing $Ga(NO_3)_3$, $KNO_3$, $Ce(NO_3)_3.6H_2O$, and $Pt(NH_3)_4(NO_3)_2$ by incipient wetness. The catalyst was dried in air at room temperature for at least 1 hour and calcined in air at 750° C. for 1 hour.

Catalyst A7 was made by impregnation of a silica-alumina support containing 20 wt. % silica (Sasol Siralox 20) with an aqueous solution containing $Ga(NO_3)_3$, $KNO_3$, $Ce(NO_3)_3.6H_2O$, and $Pt(NH_3)_4(NO_3)_2$ by incipient wetness. The catalyst was dried in air at room temperature for at least one hour and calcined in air at 750° C. for 1 hour.

Catalyst A8 was made by impregnation of a silica-alumina support containing 30 wt. % silica (Sasol Siralox 30) with an aqueous solution containing $Ga(NO_3)_3$, $KNO_3$, $Ce(NO_3)_3.6H_2O$, and $Pt(NH_3)_4(NO_3)_2$ by incipient wetness. The catalyst was dried in air at room temperature for at least 1 hour and calcined in air at 750° C. for 1 hour.

Catalyst A9 was made by impregnation of a silica-alumina support containing 40 wt. % silica (Sasol Siralox 40) with an aqueous solution containing $Ga(NO_3)_3$, $KNO_3$, $Ce(NO_3)_3.6H_2O$, and $Pt(NH_3)_4(NO_3)_2$ by incipient wetness. The catalyst was dried in air at room temperature for at least 1 hour and calcined in air at 750° C. for 1 hour.

A gallium-impregnated silica-alumina support was prepared by peptization and extrusion: 4.5 g $H_2O$, 1.0-3.0 g of an aqueous 10 wt. % gallium solution, and 3 g of concentrated $C_2H_4O_2$ was added to 13.3 g of a mixture including 90 wt. % aluminum hydroxide and 10 wt. % silica (Sasol SIRAL 10) and thoroughly mixed until visibly homogeneous. The mixture was extruded into cylindrical extrudates, dried in air at 120° C. for 4 hours, and calcined in air at 670° C. for 4 hours to provide a silica-alumina support containing 2 wt. % gallium. Catalyst A10 was made by further impregnation of the gallium-impregnated silica-alumina support with an aqueous solution containing $KNO_3$, $Ce(NO_3)_3$ and $Pt(NH_3)_4(NO_3)_2$ by incipient wetness. The catalyst was dried in air at 120° C. for 4 hours and calcined in air at 640° C. for 4 hours.

A gallium- and cerium-impregnated silica-alumina support was prepared by peptization and extrusion: 4.5 g $H_2O$, 1.0-3.0 g of an aqueous 10 wt. % gallium solution, 1.0-4.0 g of an aqueous 10 wt. % $Ce(NO_3)_3$ solution, and 3 g of concentrated $C_2H_4O_2$ was added to 13.3 g of a mixture including 90 wt. % aluminum hydroxide and 10 wt. % silica (Saslo SIRAL 10) and thoroughly mixed until visibly homogeneous. The mixture was extruded into cylindrical extrudates, dried in air at 120° C. for 4 hours, and calcined in air at 670° C. for 4 hours to provide a silica-alumina support containing 3 wt. % gallium and 2 wt. % cerium. Catalyst A11 was made by further impregnation of the gallium- and cerium-impregnated support with an aqueous solution containing $KNO_3$ and $Pt(NH_3)_4(NO_3)_2$ by incipient wetness. The catalyst was dried in air at 120° C. for 4 hours and calcined in air at 640° C. for 4 hours.

Catalyst A12 was made by impregnation of a silica-alumina support containing 1.5% $SiO_2$ (Sasol SIRALOX 1) with an aqueous solution containing $Ga(NO_3)_3$, $KNO_3$, $Pt(NH_3)_4(NO_3)_2$, $Ce(NO_3)_3$ and $Ba(NO_3)_2$ by incipient wetness. The catalyst was dried in air at room temperature for at least 1 hour and calcined in air at 750° C. for 1 hour.

Catalyst A13 was made by impregnation of a silica-alumina support containing 10% $SiO_2$ (Sasol SIRALOX 10)

with an aqueous solution containing Ga(NO$_3$)$_3$, KNO$_3$, Pt(NH$_3$)$_4$(NO$_3$)$_2$, Ce(NO$_3$)$_3$ and La(NO$_3$)$_3$ by incipient wetness. The catalyst was dried in air at room temperature for at least 1 hour and calcined in air at 750° C. for 1 hour.

Catalyst A14 was made by impregnation of a silica-alumina support containing 1.5% SiO$_2$ (Sasol SIRALOX 1) with an aqueous solution containing Ga(NO$_3$)$_3$, KNO$_3$, Pt(NH$_3$)$_4$(NO$_3$)$_2$, Ce(NO$_3$)$_3$ and Ba(NO$_3$)$_2$ by incipient wetness. The catalyst was dried in air at room temperature for at least 1 hour and calcined in air at 750° C. for 1 hour.

Catalyst A15 was made by impregnation of a silica-alumina support containing 5% SiO$_2$ (Sasol SIRALOX 5) with an aqueous solution containing Ga(NO$_3$)$_3$, KNO$_3$, Pt(NH$_3$)$_4$(NO$_3$)$_2$, Ce(NO$_3$)$_3$ and Ba(NO$_3$)$_2$ by incipient wetness. The catalyst was dried in air at room temperature for at least 1 hour and calcined in air at 750° C. for 1 hour.

A comparative alumina-supported chromium catalyst C was prepared according to conventional methods.

TABLE 1

Catalyst Compositions

| Cat. | SiO$_2$ (wt. %) | Al$_2$O$_3$ (wt. %) | Ga (wt. %) | La (wt. %) | Ce (wt. %) | Pt (ppm) | K (wt. %) | Ba (wt. %) |
|---|---|---|---|---|---|---|---|---|
| A1 | 10 | 90 | 3.0 | 0 | 2.0 | 200 | 0.25 | 0 |
| A2 | 25 | 75 | 4.5 | 0 | 1.0 | 200 | 0.25 | 0 |
| A3 | 5 | 95 | 4.5 | 0 | 1.0 | 200 | 0.25 | 0 |
| A4 | 5 | 95 | 3.0 | 0 | 1.0 | 200 | 0.25 | 0 |
| A5 | 10 | 90 | 4.5 | 0 | 1.0 | 200 | 0.25 | 0 |
| A6 | 10 | 90 | 4.5 | 0 | 2.0 | 200 | 0.25 | 0 |
| A7 | 20 | 80 | 4.5 | 0 | 3.0 | 200 | 0.25 | 0 |
| A8 | 30 | 70 | 4.5 | 0 | 1.0 | 200 | 0.25 | 0 |
| A9 | 40 | 60 | 4.5 | 0 | 1.0 | 200 | 0.25 | 0 |
| A10 | 9.8 | 88.2 | 2 | 0 | 1.0 | 250 | 1.0 | 0 |
| A11 | 9.6 | 86.4 | 3 | 0 | 1.0 | 250 | 0.35 | 0 |
| A12 | 1.5 | 98.5 | 4.5 | 0 | 1.0 | 200 | 0.25 | 1 |
| A13 | 10 | 90 | 4.5 | 1 | 1.0 | 200 | 0.25 | 0 |
| A14 | 1.5 | 98.5 | 3.0 | 0 | 1.0. | 200 | 0.25 | 1 |
| A15 | 5 | 95 | 4.5 | 0 | 1.0 | 200 | 0.25 | 1 |

Example 2. Propane Dehydrogenation

Catalyst compositions prepared according to Example 1 were tested as prepared in a fixed-bed reactor. A feed containing 100 mol. % propane was passed over a catalyst bed at a total pressure of 0.5 atm., at 2.0 h$^{-1}$ liquid hourly space velocity (LHSV), at a temperature within the range of 540-600° C. in cyclic mode, where 10 minutes of propane dehydrogenation is followed by catalyst regeneration in air. Results are provided in Table 2 below.

TABLE 2

Propane Dehydrogenation

| Cat. | T (° C.) | Conversion (wt. %) | Selectivity (wt. %) | Yield (wt. %) |
|---|---|---|---|---|
| C | 540 | 33.04 | 87.02 | 28.75 |
| C | 570 | 46.29 | 84.06 | 38.94 |
| C | 600 | 58.7 | 78.25 | 45.91 |
| A1 | 540 | 27.8 | 91.1 | 25.3 |
| A1 | 570 | 34.7 | 89.9 | 31.2 |
| A1 | 600 | 43.2 | 87.2 | 37.7 |
| A2 | 540 | 34.5 | 91.4 | 31.6 |
| A2 | 570 | 46.4 | 88.7 | 41.1 |
| A2 | 600 | 58.1 | 84.9 | 49.3 |
| A3 | 540 | 34.9 | 90.5 | 31.5 |
| A3 | 570 | 42.8 | 88.6 | 37.9 |

TABLE 2-continued

Propane Dehydrogenation

| Cat. | T (° C.) | Conversion (wt. %) | Selectivity (wt. %) | Yield (wt. %) |
|---|---|---|---|---|
| A3 | 600 | 51.1 | 84.2 | 43 |
| A4 | 540 | 33.2 | 91.6 | 30.4 |
| A4 | 570 | 40.6 | 90.3 | 36.6 |
| A4 | 600 | 48.7 | 86.7 | 42.2 |
| A5 | 540 | 36.48 | 89.72 | 32.72 |
| A5 | 570 | 46.79 | 88.38 | 41.38 |
| A5 | 600 | 57.8 | 84.23 | 48.67 |
| A6 | 540 | 36.12 | 91.02 | 32.88 |
| A6 | 570 | 45.23 | 89.4 | 40.45 |
| A6 | 600 | 55.19 | 84.74 | 46.74 |
| A7 | 540 | 31.88 | 90.73 | 28.91 |
| A7 | 570 | 41.41 | 89.63 | 37.13 |
| A7 | 600 | 51.64 | 86.87 | 44.83 |
| A8 | 540 | 37.53 | 88.05 | 33.05 |
| A8 | 570 | 47.77 | 87.23 | 41.68 |
| A8 | 600 | 58.59 | 83.99 | 49.2 |
| A9 | 540 | 36.85 | 88.95 | 32.79 |
| A9 | 570 | 46.45 | 88.26 | 41.01 |
| A9 | 600 | 56.61 | 84.26 | 47.7 |
| A10 | 540 | 27.6 | 93.4 | 25.6 |
| A10 | 570 | 32.0 | 92.2 | 29.5 |
| A10 | 600 | 39.1 | 89.7 | 35.1 |
| A11 | 540 | 36.1 | 87.5 | 31.6 |
| A11 | 570 | 44.2 | 84.9 | 37.5 |
| A11 | 600 | 52.5 | 79.4 | 41.7 |
| A12 | 540 | 15.6 | 90.2 | 13.9 |
| A12 | 570 | 20.9 | 90.1 | 18.9 |
| A12 | 600 | 29.3 | 86.1 | 25.1 |
| A13 | 540 | 35.4 | 91.3 | 32.3 |
| A13 | 570 | 47.3 | 89.3 | 42.3 |
| A13 | 600 | 55.3 | 85.8 | 47.5 |
| A14 | 540 | 17.6 | 89.9 | 15.8 |
| A14 | 570 | 20.5 | 87.3 | 17.9 |
| A14 | 600 | 35.1 | 84.5 | 29.7 |
| A15 | 540 | 35.2 | 91.5 | 32.2 |
| A15 | 570 | 45.4 | 90.3 | 41.0 |
| A15 | 600 | 54.6 | 87.2 | 47.6 |

The results show that the performance of the catalysts tested was acceptable, providing good yields, selectivity and conversion even in the absence of chromium.

What is claimed is:

1. A calcined dehydrogenation catalyst comprising
  a primary species P1 selected from the group consisting of Ga, In, Tl, Ge, Sn, and Pb and combinations thereof, present in the composition in an amount within the range of about 0.05 wt. % to about 20 wt. %, calculated as elemental metal on a calcined basis;
  a primary species P2 selected from the lanthanides, present in the composition in an amount within the range of about 0.05 wt. % to about 10 wt. %, calculated as elemental metal on a calcined basis;
  a promoter M1 selected from the group consisting of Ni, Pd, and Pt, present in the composition in an amount within the range of about 10 ppm to about 500 ppm, calculated as elemental metal on a calcined basis;
  a promoter M2 selected from the group consisting of Li, Na, K, Rb, Cs, Be, Mg, Ca, Sr, and Ba, present in the composition in an amount within the range of about 0.05 wt. % to about 3 wt. %, calculated as elemental metal on a calcined basis; and
  a silica-alumina supports S1, present in the composition in an amount within the range of about 60 wt. % to about 99 wt. %, calculated as oxide on a calcined basis;
wherein the amount of silica present in S1 is within the range of about 5 wt. % to about 70 wt. % of S1.

2. The catalyst composition of claim 1, wherein P1 is selected from Ga, Ge, In, Sn, and Tl and combinations thereof.

3. The catalyst composition of claim 1, wherein P1 is Ga.

4. The catalyst composition of claim 1, wherein P1 is present in the composition in an amount within the range of about 0.1 wt. % to about 10 wt. %, calculated as elemental metal on a calcined basis.

5. The catalyst composition of claim 1, wherein M1 is selected from Pd and Pt.

6. The catalyst composition of claim 1, wherein M1 is present in the composition in an amount within the range of about 50 ppm to about 400 ppm, calculated as elemental metal on a calcined weight basis.

7. The catalyst composition of claim 1, wherein M2 is selected from Li, Na, K, Cs, and Ba.

8. The catalyst composition of claim 1, wherein M2 is present in the composition in an amount within the range of about 0.05 wt. % to about 2 wt. %, calculated as elemental metal on a calcined basis.

9. The catalyst composition of claim 1, wherein
P1 is Ga, present in the composition in an amount within the range of about 0.1 wt. % to about 10 wt. %, calculated as elemental metal on a calcined basis;
P2 is Ce, present in the composition in an amount within the range of about 0.1 wt. % to about 6 wt. %, calculated as elemental metal on a calcined basis; and
M1 is Pt, present in the composition in an amount within the range of about 50 ppm to about 400 ppm, calculated as elemental metal on a calcined weight basis.

10. A method for preparing a dehydrogenation catalyst composition according to claim 1, comprising
providing a silica-alumina support S1, optionally formulated with one or more of P1, P2, M1, and M2;
impregnating the silica-alumina support S1 with one or more of P1, P2, M1 and M2 in one or more impregnation steps, each impregnation step comprising contacting the support with an impregnation solution comprising one or more of a P1 source, a P2 source, an M1 source and an M2 source; and
calcining the impregnated silica-alumina support S1.

11. A method according to claim 10, wherein providing a silica-alumina support S1 comprises reacting an S1 source.

12. A method for preparing a dehydrogenation catalyst composition according to claim 1, comprising
providing a silica-alumina support S1 formulated with Ga;
impregnating the Ga-formulated silica-alumina support S1 with an impregnation solution comprising a P2 source, an M1 source and an M2 source, wherein if Ce is present in the dehydrogenation catalyst, the impregnation solution includes one or more of Ba and La; and
calcining the impregnated Ga-formulated silica-alumina support S1.

13. A method according to claim 12, wherein the P2 source is a salt.

14. A method for dehydrogenating hydrocarbons, the method comprising contacting a hydrocarbon feed with the catalyst composition of claim 1.

15. A method according to claim 14, wherein the hydrocarbon feed comprises one or more $C_3$-$C_5$ alkanes.

16. A method according to claim 13, wherein the P2 source is $Ce(NO_3)_3$ or $La(NO_3)_3$.

17. The catalyst composition of claim 1, wherein P2 is selected from La, Ce, and Nd.

18. The catalyst composition of claim 1, wherein P2 is Ce, present in the composition in an amount within the range of about 0.1 wt. % to about 6 wt. %.

19. The catalyst composition of claim 1, wherein the amount of silica present in S1 is within the range of 10 wt. % to about 70 wt. % of S1.

20. A method according to claim 14, carried out at a temperature within the range of about 400° C. to about 750° C.

* * * * *